US00PP33569P3

(12) United States Plant Patent
Galan

(10) Patent No.: US PP33,569 P3
(45) Date of Patent: Oct. 19, 2021

(54) ***ALLIUM* PLANT NAMED 'BERALJAS'**

(50) Latin Name: ***Allium ampeloprasum* L.**
Varietal Denomination: BERALJAS

(71) Applicant: J.M. van Berkel B.V., Hillegom (NL)

(72) Inventor: Joaquin Acosta Galan, Chipiona (ES)

(73) Assignee: J.M. van Berkel B.V., Hillegom (NL)

( * ) Notice: Subject to any disclaimer, the term of this patent is extended or adjusted under 35 U.S.C. 154(b) by 0 days.

(21) Appl. No.: 16/602,317

(22) Filed: Sep. 12, 2019

(65) Prior Publication Data

US 2020/0084948 P1 Mar. 12, 2020

(51) Int. Cl.
*A01H 5/02* (2018.01)
*A01H 6/04* (2018.01)

(52) U.S. Cl.
USPC ..... Plt./263.1
CPC ..... *A01H 6/04* (2018.05)

(58) Field of Classification Search
USPC ..... Plt./263.1
CPC ..... A01H 6/04
See application file for complete search history.

(56) References Cited

PUBLICATIONS

*Allium*, Garden Onion, Edible Onion 'Jasmine', downloaded from https://davesgarden.com/guides/pf/go/200188/#b, downloaded on Mar. 3, 2021.*

Pluto database hit on UPOV Plant Variety Rights on an *Allium* plant named 'Jasmine', QZ PBR 57850, grant publcation date Jun. 16, 2021.*

* cited by examiner

*Primary Examiner* — Anne Marie Grunberg
(74) *Attorney, Agent, or Firm* — Samuel R. McCoy, Jr.

(57) ABSTRACT

'BERALJAS' is a new and distinctive variety of *Allium* plant which is characterized by umbels with a large quantity of pink flowers and a late flowering season.

1 Drawing Sheet

Latin name of the genus and species: The Latin name of the novel variety disclosed herein is *Allium ampeloprasum* L.

Variety denomination: The inventive variety of *Allium* disclosed herein has been given the variety denomination 'BERALJAS'.

CROSS REFERENCE TO RELATED APPLICATIONS

None.

BACKGROUND OF THE INVENTION

Parentage: 'BERALJAS' is a product of chance discovery by the inventor. In 2017, the inventor discovered the new plant at a commercial nursery in Chipiona, Spain, growing in a landscaped area adjacent to fields where a plurality of cultivated populations of *Allium* sp. plants are grown, including *Allium ampeloprasum* seedlings and *Allium* sp. 'Summer Drummer'. The exact parentage is unknown. The new plant was noted for its pink umbels and was subsequently isolated for further evaluation in order to confirm the distinctness and stability of the characteristics first observed. Upon confirmation of distinctness and stability, 'BERALJAS' was selected for commercialization.

Asexual Reproduction: Asexual reproduction of the new cultivar 'BERALJAS', by way of bulb division, was first initiated in June of 2017 at a commercial greenhouse in Chipiona, Spain. Through two subsequent generations, the unique features of this cultivar have proven to be stable and true to type.

SUMMARY OF THE INVENTION

The following traits have been repeatedly observed and represent the characteristics of the new cultivar. The characteristics in combination distinguish 'BERALJAS' as a distinct cultivar of *Allium*.

1. 'BERALJAS' exhibits umbels with a large quantity of pink flowers; and
2. 'BERALJAS' exhibits a late flowering season.

BRIEF DESCRIPTION OF THE DRAWINGS

The FIGURE shows as true as is reasonably possible to obtain in color photographs of this type, an exemplary umbel of 'BERALJAS'.

DETAILED BOTANICAL DESCRIPTION OF THE VARIETY

The following observations and measurements made in August of 2018 describe averages from a sample set of six specimens of 12 months old 'BERALJAS' field-grown plants produced at commercial nursery in Hillegom, the Netherlands. Plants were produced using conventional field production protocols for *Allium* which consisted of regular overhead irrigation and no fertilizer or pesticide applications. During the production period, nighttime temperatures ranged from 12 to 22 degrees Celsius and high daytime temperatures ranged between 20 to 35 degrees Celsius. Plants were grown in full sun and no photoperiodic treatments or artificial light was given to the plants.

Those skilled in the art will appreciate that certain characteristics will vary with older or, conversely, with younger plants. 'BERALJAS' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'BERALJAS' and a comparison with the closest known comparator is provided below.

General plant description:

*Growth habit*.—Succulent perennial with foliage growing in a non-branched basal rosette.

*Plant shape*.—Flattened globular.

*Height from soil level to top of foliar plane*.—9.3 cm.

*Plant spread*.—Average of 20.0 cm.

*Growth rate*.—Moderate.

*Plant vigor*.—Moderate.

*Propagation method*.—Bulb division.

*Disease and pest resistance or susceptibility*.—Neither resistance nor susceptibility to typical *Allium* pests and diseases has been observed.

*Environmental tolerances*.—Adapt to, at least, USDA Zones 6 to 10 and temperatures as high as 40 degrees Celsius and as low as negative 23 degrees Celsius; moderate tolerance to wind and rain.

Roots:

*General*.—The roots are bulbous and bear fibrous roots from the base, similar to other *Allium*.

*Bulb dimensions*.—4.0 cm long and 4.7 cm in diameter.

*Texture and luster of bulbs*.—Smooth, glabrous and slightly glossy.

*Bulb color*.—White, nearest to in between RHS NN155A and NN155B.

Stem:

*Branching habit*.—Acaulescent, bulbous plant with shoots emerging from bulbs with an upright attitude.

Foliage:

*Quantity*.—Typically 4 to 5 leaves per bulb.

*Arrangement*.—Basally alternate.

*Attachment*.—Sessile.

*Division*.—Simple.

*Attitude*.—The proximal portion of the foliage is upright and outward, while the distal portion is pendulous.

*Fragrance*.—Strongly aromatic, typical of *Allium* sp.

*Lamina*.—Shape — Linear. Aspect — Concave and axially twisted. Apex — Acute. Base — Truncate. Margins — Entire. Texture and luster — Smooth, glabrous, and matte on both the adaxial and abaxial surfaces. Mature leaf dimensions — 14.5 cm long and 0.9 cm wide. Mature leaf color — Adaxial surface — Yellow-green, nearest to RHS 137A. Abaxial surface — Yellow-green, nearest to RHS 137B. Venation — Type — Parallel. Color, adaxial surface — Yellow-green, nearest to RHS 137A. Color, abaxial surface — Yellow-green, nearest to RHS 137B.

Inflorescence:

*Inflorescence type*.—Umbel.

*Natural flowering season*.—Spring into summer in Hillegom, the Netherlands.

*Time to flower*.—Approximately 11 months after flowering.

*Dimensions*.—12.4 cm high, not including peduncle, and 12.5 cm in diameter.

*Quantity of inflorescence per bulb*.—1.

*Quantity of open flowers and buds per inflorescence*.—570.

*Quantity of open flowers per plant*.—500.

*Quantity of buds per plants*.—70.

*Attitude*.—Upright.

*Peduncles*.—Length — Average of 83 cm. Diameter — Average of 0.7 cm. Attitude — Nearly vertical. Strength — Strong. Texture and luster — Smooth, glabrous and slightly glossy. Color — Yellow-green, nearest to RHS 144A, and aging to greyed-yellow at anthesis, nearest the RHS 162B.

Buds:

*Shape*.—Obelliptic.

*Dimensions*.—5.0 mm long and 4.0 mm in diameter.

*Color*.—Purple, nearest to RHS 76B, and fading lighter towards the base, nearest to RHS 76D.

*Texture*.—Smooth and glabrous.

*Luster*.—Moderately glossy.

Flowers:

*Form*.—Cam panulate, with an inner whorl of tepals and an outer whorl of tepals.

*Attitude*.—Outward in all directions, depending on position in the umbel.

*Lastingness*.—Approximately 21 days.

*Persistence*.—Persistent; flowers are clinging.

*Fragrance*.—Moderately fragrant; a sweet perfume, typical of *Allium* sp.

*Perianth depth*.—7.0 mm.

*Perianth diameter*.—10 mm.

*Pedicels*.—Dimensions — 6.0 cm long and 0.1 cm in diameter. Strength — Moderately strong. Texture and luster — Smooth, glabrous, and moderately glossy. Color — Purple, nearest to RHS N77D.

*Tepals*.—Quantity — 6. Arrangement — Rotate; 2 whorls. Shape — Ovate. Apex — Acute to broadly acute. Base — Cuneate. Aspect — Concave. Dimensions — 5 mm long and 2.5 mm wide, as measured. Texture and luster, inner surface — Smooth, glabrous, and moderately glossy. Texture and luster, outer surface — Smooth, glabrous, and matte. Margin — Entire; no undulation. Color when opening, inner tepals — Inner surface — White, nearest to RHS N155A, and lightly suffused with purple, nearest to RHS 76C. Main vein is green, nearest to RHS 137B. Outer surface — Purple, nearest to RHS 76D. Main vein is green, nearest to RHS 137B. Color when opening, outer tepals — Inner surface — Purple, nearest to RHS 76B. Main vein is green, nearest to RHS 137A. Outer surface — Purple, nearest to RHS 75A. Main vein is green, nearest to RHS 137B. Color when fully opened, inner tepals — Inner surface — White, nearest to RHS N155A, and lightly suffused with purple, nearest to RHS 76C. Outer surface — Purple, nearest to RHS 76D. Venation, inner surface — Green, RHS 137B. Venation, outer surface — Green, RHS 137A. Color when fully opened, outer tepals — Inner surface — Purple, nearest to RHS 76B. Outer surface — Purple, nearest to RHS 75A. Venation, inner surface — Green, RHS 137B. Venation, outer surface — Green, RHS 137A.

Reproductive organs:

*Stamens*.—Quantity — 6. Anthers — Attachment — Dorsifixed. Shape — Narrowly oblong. Dimensions — Approximately 1.0 mm long and 0.5 mm wide. Color — Black, nearest to RHS 203A. Filaments — Cross-section — Flattened. Length — 6.0 mm. Width — 2.5 cm. Color — White, nearest to RHS NN155D. Pollen, amount — Moderately abundant. Pollen color — White, nearest to RHS 155D.

*Pistil*.—Quantity — 1. Length — 4.0 mm. Style — Length — 3.5 mm. Color — White, nearest to RHS NN155D. Stigma — Shape — Pointed. Length — 0.5 mm. Diameter — 0.5 mm. Color — White, nearest to RHS NN155D. Ovary Color — Yellow-green, nearest to RHS 144B.

Fruit and seeds: Not observed.

COMPARISONS WITH THE PARENT PLANTS

'BERALJAS' is the product of chance discovery and the parentage is unknown. Therefore, a comparison is not possible.

COMPARISONS WITH THE CLOSEST KNOWN COMMERCIAL COMPARATOR

Plants of the new cultivar 'BERALJAS' differ from the closest known commercial comparator, *Allium* sp. 'Summer Drummer' (Netherlands Plant Breeder's Rights grant number 30654), in the following characteristics described in Table 1 below.

TABLE 1

| Characteristic | 'BERALJAS' | 'Summer Drummer' |
|---|---|---|
| Plant size. | Smaller than 'Summer Drummer'. | Larger than 'BERALJAS'. |
| Umbel size. | Smaller than 'Summer Drummer'. | Larger than 'BERALJAS'. |
| General coloration of the tepals. | Light purple, generally appearing as pink. | Darker purple, generally appearing as dark pink to red-purple. |

That which is claimed is:

1. A new and distinct *Allium* plant named 'BERALJAS', substantially as described and illustrated herein.

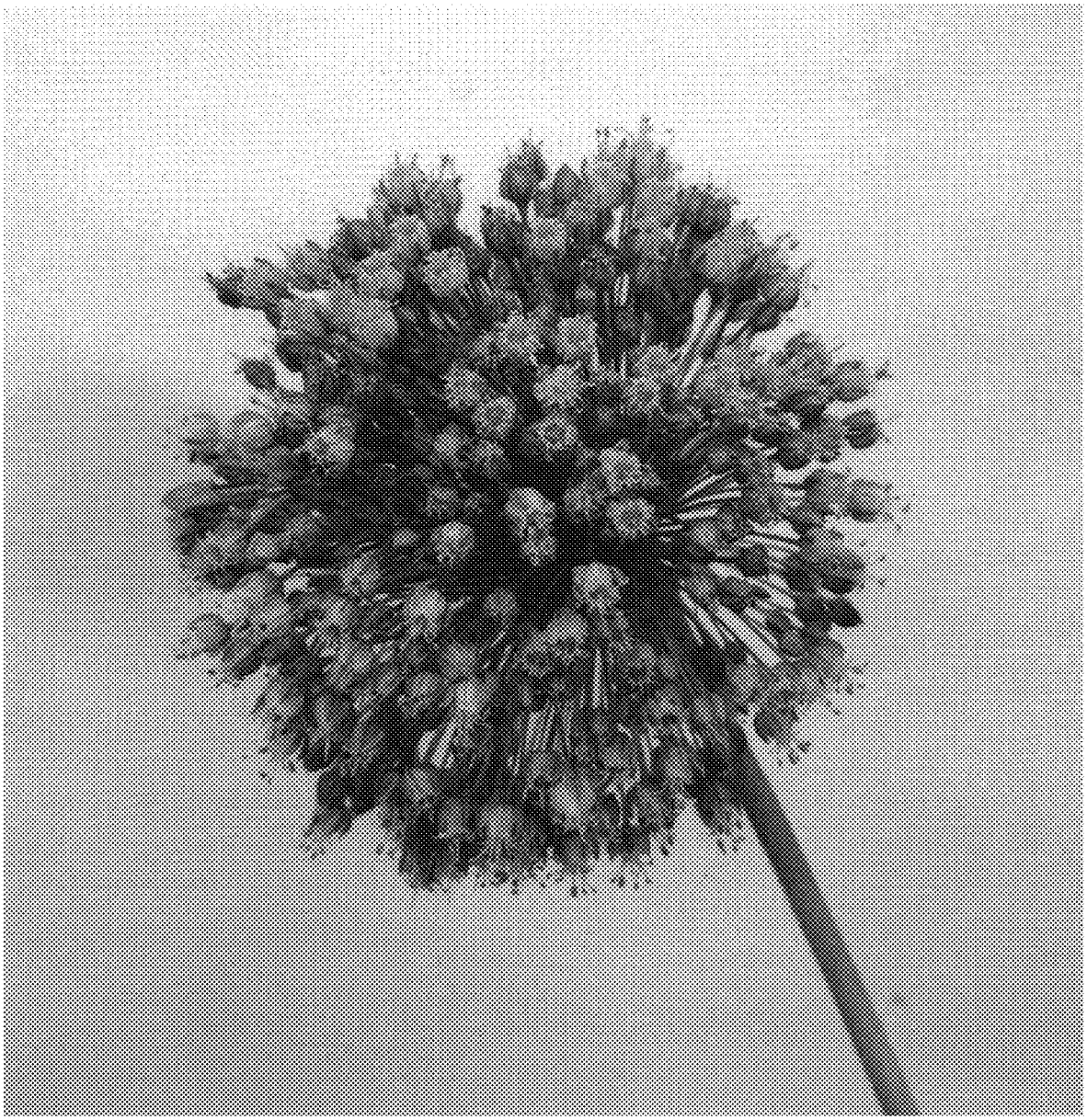

* * * * *